United States Patent [19]
Peppel et al.

[11] Patent Number: 5,342,326
[45] Date of Patent: Aug. 30, 1994

[54] CAPLESS MEDICAL VALVE

[75] Inventors: Peter Peppel, Nazareth; Kenneth C. Raines, Bethlehem, both of Pa.

[73] Assignee: B. Braun Medical, Inc., Bethlehem, Pa.

[21] Appl. No.: 124,640

[22] Filed: Sep. 22, 1993

[51] Int. Cl.$^5$ .............................................. A61M 25/00
[52] U.S. Cl. .................................... 604/284; 604/164; 604/247
[58] Field of Search ................. 604/283, 284, 247, 83, 604/249, 256, 30, 905, 167, 169

[56] References Cited

U.S. PATENT DOCUMENTS

| | | | |
|---|---|---|---|
| 4,683,916 | 8/1987 | Raines | 604/247 X |
| 4,883,456 | 11/1989 | Holter | 604/247 X |
| 5,006,114 | 4/1991 | Rogers et al. | 604/167 |
| 5,242,432 | 9/1993 | De Frank | 604/247 X |

*Primary Examiner*—John D. Yasko
*Attorney, Agent, or Firm*—Shoemaker and Mattare, Ltd.

[57] ABSTRACT

A capless medical valve includes a housing defining an inlet, an outlet, and a valve bore, all three of which meet at a common transition zone bounded by a transition surface. A valve member confined within the valve bore has a spherical head and a generally cylindrical stem sized to fit within the inlet and extending from the head toward the transition zone. A spring in compression biases the valve member toward the inlet, so that the spherical head is normally seated against the transition surface, but can be mechanically displaced off its seat by inserting a syringe tip or fitting into the inlet.

17 Claims, 3 Drawing Sheets

CAPLESS MEDICAL VALVE

BACKGROUND OF THE INVENTION

This invention relates generally to fluid handling and more particularly to a capless medical valve.

Needleless injection ports, installed in an infusion line, allow medical personnel to administer medications to patients occasionally through the already-installed infusion line. To be safe and effective, a needleless injection port must prevent leakage of intravenous fluid out of the port while it is idle, and must absolutely prevent air or other matter from entering the infusion line accidentally. The injection port should not have recesses which could harbor microbes, and it is convenient if contamination can be prevented without requiring a separate cap.

A number of capless medical valves are known, including that shown in U.S. Pat. No. 5,006,114. That valve has a member which can be depressed to open a flowpath when a syringe tip is pushed into the valve body; however, it is necessary to give an irregular surface to either the end of the syringe tip or to the valve plunger. Were both surfaces to be planar, the mating surfaces could work together as a seal, preventing—or at least throttling—flow out of the syringe. Irregularities like the bumps described in the above patent have a disadvantages of more difficult manufacture, and of making surfaces harder to clean. It is not practical to provide special syringes with irregular tip surfaces for just this one use, and it is preferred that the needleless valve have only smooth surfaces, so that it can be cleaned easily by wiping.

SUMMARY OF THE INVENTION

An object of the invention is to provide an injection port or valve having a flat, wipeable surface at the injection locus.

Another object of the invention is construct a valve that avoids restricting flow through a medical injection port.

A further object of the invention is to provide a valve that is simple, and economical to manufacture.

These and other objects are attained by a capless medical valve which includes a housing defining an inlet, an outlet, and a valve bore, all three of which meet at a common transition zone bounded by a transition surface. A valve member confined within the valve bore has a spherical head and a generally cylindrical stem sized to fit within the inlet and extending from the head toward the transition zone. A spring in compression biases the valve member toward the inlet, so that the spherical head is normally seated against the transition surface, but can be mechanically displaced off its seat by inserting a syringe tip or fitting into the inlet.

BRIEF DESCRIPTION OF THE DRAWINGS

In the accompanying drawings.

DESCRIPTION OF THE PREFERRED EMBODIMENT

Figure 1:
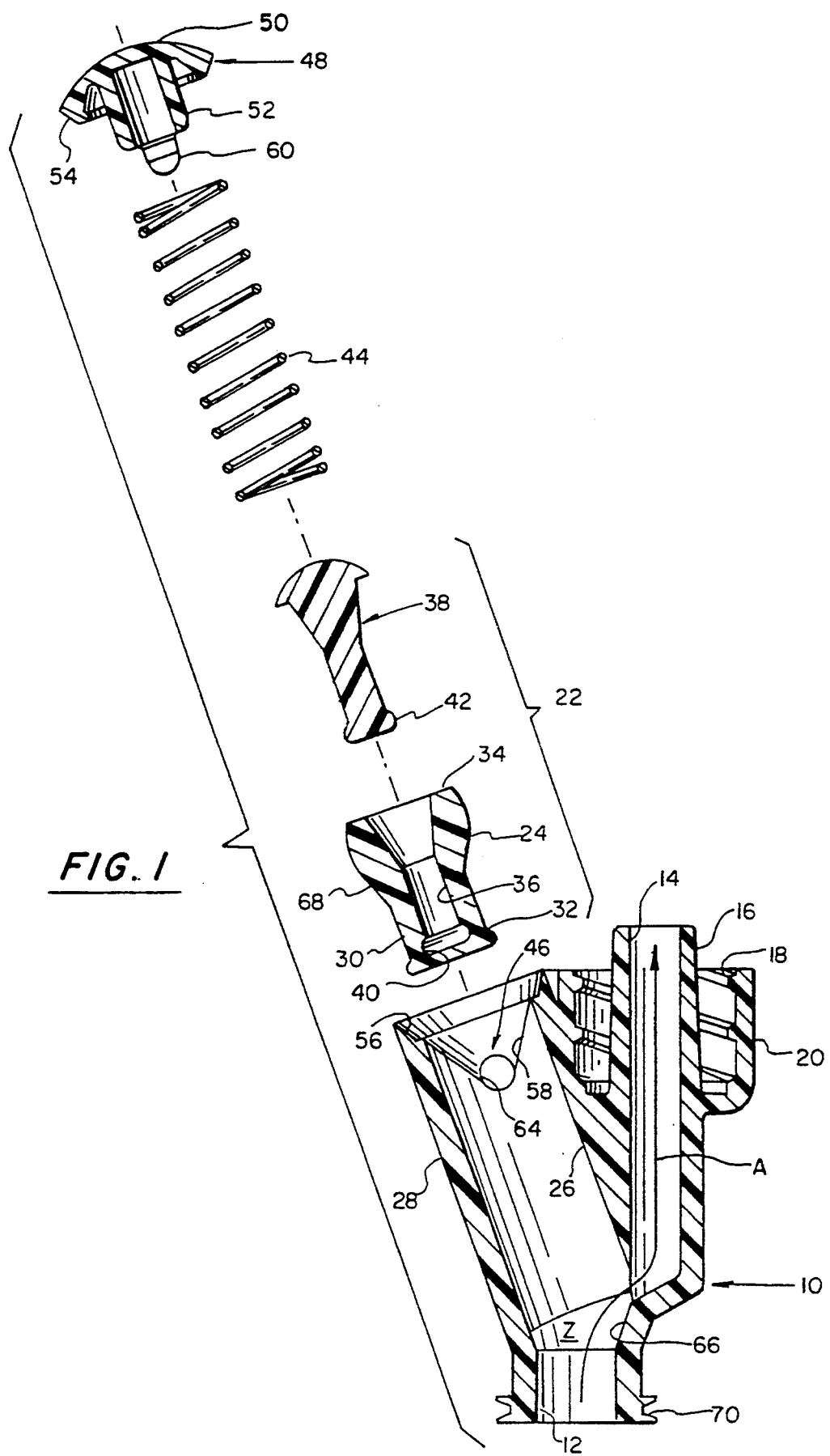
FIG. 1 is an exploded sectional view of a capless medical valve embodying the invention, taken on a vertical plane of symmetry.

A capless medical valve embodying the invention includes a Y-shaped housing 10, which is preferably injection molded from a suitable polymeric material. The body has an inlet port 12 at the bottom, and an outlet port 14 provided with a tapered luer fitting 16 surrounded by internal threads 18 in a skirt 20. The flowpath is designated in FIG. 1 by an arrow "A" running from the inlet (upstream) through the outlet (downstream). Externally, the flowpath is represented by a graphic arrow 21, a portion of which appears in FIG. 2, embossed or printed on one or both faces of the housing. The arrow 21 is aesthetically pleasing, and advises the user of the flow direction.

Flow through the valve is controlled by a mushroom-shaped valve member 22, whose head 24 is confined within an inclined cylindrical bore 26 of about the same diameter as the head, in the other arm 28 of the "Y". The stem 30 of the valve member has an rounded, radially extending circumferential rib 32 at its bottom edge. This rib seals against the mouth of the inlet port when the valve is closed (FIG. 2), with its flat bottom surface 33 flush with the bottom surface 35 of the housing, thus presenting a wipeable surface which does not tend to accumulate foreign matter.

The head 24 of the valve member is generally spherical, but has a truncated upper end 34 and a central blind bore 36 into which a plug 38 is pressed. A groove 40 at the bottom of the bore engages a rib 42 at the bottom of the plug, to retain the plug. The plug is of a harder material than is the body of the valve member; it reinforces or stiffens the softer surrounding material, which must be much softer to provide proper sealing. The top of the plug is continuous with the spherical surface of the body member.

The valve member 22 is biased towards its normally closed configuration by a compression coil spring 44 that bears against the hard material of the plug 38. The spring's free length and binding height are chosen so that the member is biased downward at all points in its travel between its seated position (FIG. 2) and a position (FIG. 3) in which the the valve member is substantially out of the flow path, and the bottom surface is at a substantial angle to the end surface of the syring tip, so that fluid can flow freely from the syringe.

Figure 5:
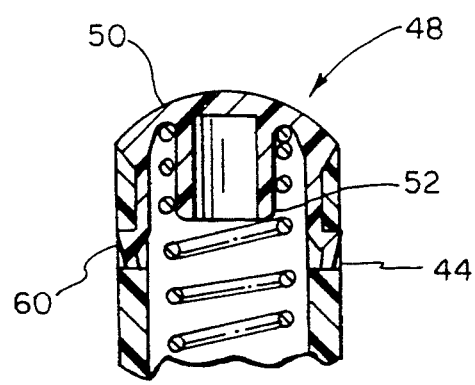
FIG. 5 is a sectional view, taken on a plane perpendicular to the section plane of FIG. 1, showing a portion of the spring and its retainer, assembled.
Figure 4:
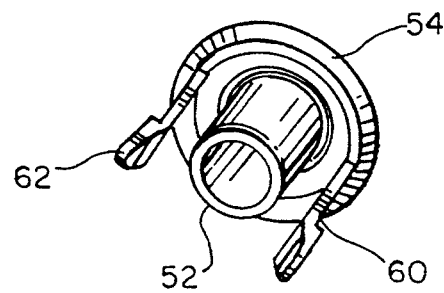
FIG. 4 is a detailed perspective view of the bottom of a spring retainer.

The spring is inserted from the open top end 46 of the bore 26, followed by a retainer 48, best seen in FIGS. 4 and 5. The retainer has a domed top surface 50 overlying a tubular spring post 52. The rim of the retainer has an beveled surface 54 that seats against a conforming counterbore 56 at the mouth of the bore 26. Two triangular recesses 58 (one of which appears in FIG. 1) are formed in the mouth below the counterbore, to provide clearance for the retainer's locking ears 60. Each of these ears has an integral button 62 at its tip, offset outward so as to snap into a like-sized hole 64 at the bottom of the corresponding recess 58, when the retainer is installed. If the retainer is not properly aligned initially, the sides of the recesses act as camming surfaces which, by engaging the ears 60, rotate the retainer to its proper position as the retainer is pushed into place.

Figure 2:
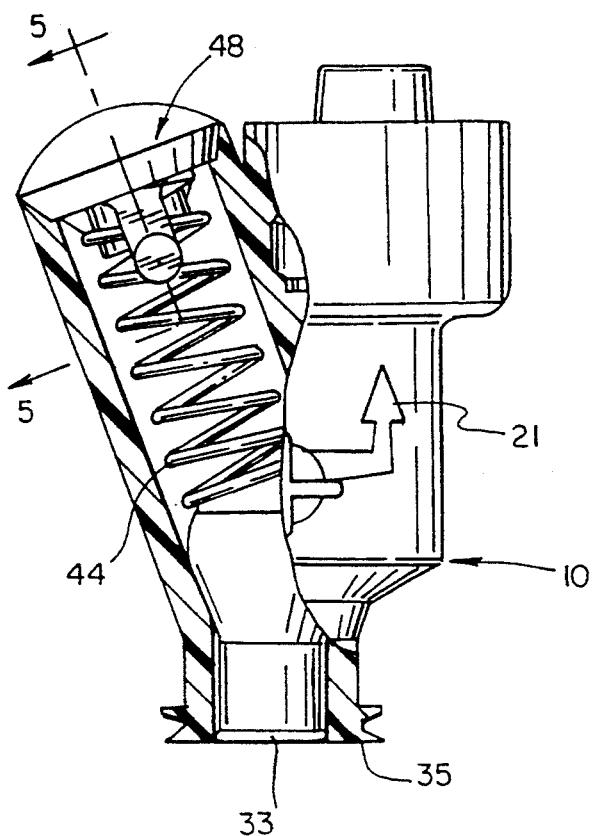
FIG. 2 is a front elevation, partially in section, of the valve in its closed configuration.

Returning to FIG. 1, one may observe a transition zone "Z" bounded by a frustoconical transition surface 66 between the inlet port, the outlet port, and the bore 26. The apex angle of the transition 66 is slightly less than that of the valve member's frustoconical surface 68, so that a seal is formed therebetween as the spring holds the valve closed (FIG. 2). The soft elastomeric material of the valve member deforms to match the shape of the surface 68. The geometry of the valve housing and the member are designed so that, while the spherical head of the valve member is always in contact with 360° of the bore 26, the stem can make the turn at the transition without interference, and is guided by the transition into the inlet 12.

Figure 3:
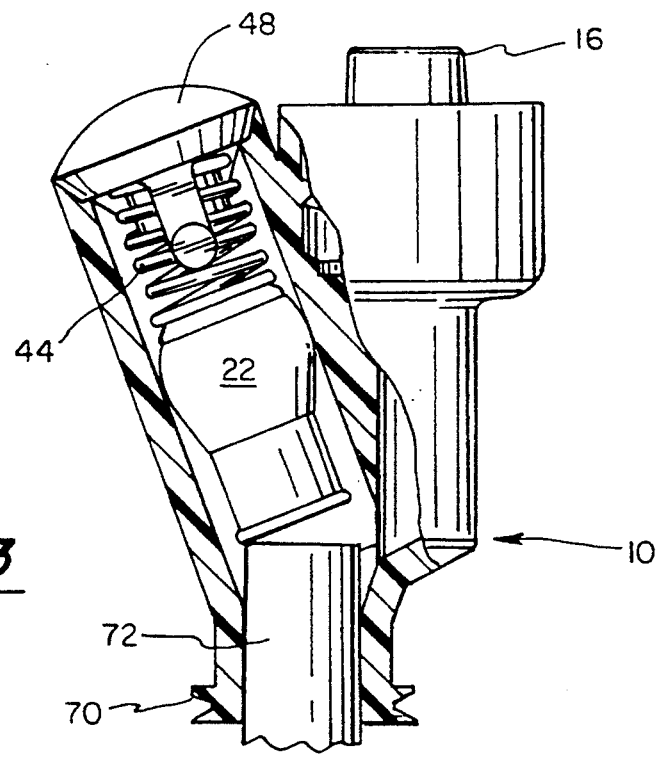
FIG. 3 is a view like FIG. 2, showing the valve open.

The bottom of the valve, around the mouth of the inlet, is provided with a male helical thread 70 onto which a suitably threaded syringe or other fitting can be screwed. Only the tip 72 of such a device is represented in FIG. 3, which illustrates how the valve member is mechanically displaced inward by the syringe tip, and pivots to open the flowpath and permit fluid to pass through the valve to the patient.

Since the invention is subject to modifications and variations, it is intended that the foregoing description and the accompanying drawings shall be interpreted as illustrative of only one form of the invention, whose scope is to be measured by the following claims.

I claim:

1. A capless medical valve comprising
a housing defining an inlet, an outlet, and a valve bore having an axis oblique to said inlet, said inlet, outlet and valve bore meeting at a common transition zone bounded by a transition surface,
a valve member confined within the valve bore, said member having a spherical head and a generally cylindrical stem sized to fit within said inlet and extending from the head toward said transition zone,
wherein the stem of the valve member has a diameter substantially less than the diameter of the spherical head, to provide clearance enabling the valve member to turn from an orientation aligned with said valve bore when the valve is open to a position aligned with said inlet when the valve is closed, and
means for biasing the valve member toward said inlet, whereby the valve is normally closed by sealing contact between said spherical head and said transition surface, but can be opened by mechanically forcing said valve member off its seat by inserting a syringe tip or fitting into the inlet.

2. The invention of claim 1, wherein the transition surface is a section of a conical surface, and is configured so that it provides a 360° seat for the spherical head when the valve is closed.

3. The invention of claim 1, wherein the valve member comprises a relatively soft lower portion including those surfaces of the member which seat against said body, and a harder core which stiffens the soft portion.

4. The invention of claim 3, wherein the core has a circumferential rib, and the soft portion has a corresponding groove that receives the rib, to secure the core within the soft portion.

5. The invention of claim 3, wherein the core has a top extending above the soft portion, and bearing against said biasing means.

6. The invention of claim 1, wherein the cylindrical stem of the valve member has a circumferential rib at its bottom end which seals against the inlet port.

7. The invention of claim 1, wherein the biasing means is a compression coil spring.

8. The invention of claim 7, further comprising a retainer cap for confining said spring to said valve bore.

9. The invention of claim 8, wherein the retainer cap includes means for centering the spring in the valve bore, and said housing and said retainer cap have means providing a snap-in connection.

10. The invention of claim 9, wherein the snap-in connection includes
a pair of axially extending ears on said retainer cap, each ear having an outward protuberance thereon, and
means within said bore for receiving said protuberances.

11. The invention of claim 10, wherein the protuberances are circular buttons, and the receiving means are corresponding holes.

12. The invention of claim 11, further comprising a pair of triangular recesses formed in the valve bore directly above the respective holes, to direct the buttons into said holes.

13. The invention of claim 1, wherein said inlet, said outlet and said valve bore are all non-colinear.

14. The invention of claim 13, wherein said inlet and said outlet extend along parallel, offset axes.

15. The invention of claim 1, further comprising a graphic arrow on the outside of the housing, said arrow extending generally along a flowpath in the direction of said outlet, to provide a visible indicator of flow direction.

16. The invention of claim 1, Wherein said inlet port and said outlet port each are surrounded by helical threads so that associated equipment may be affixed thereto.

17. The invention of claim 1, wherein the valve member has a bottom surface and the housing has a bottom surface, said surfaces being substantially coplanar when the valve is closed.

* * * * *